US00PP33127P3

(12) United States Plant Patent
Takano et al.

(10) Patent No.: US PP33,127 P3
(45) Date of Patent: Jun. 1, 2021

(54) MAITAKE MUSHROOM NAMED 'GRIFON-8GO'

(50) Latin Name: ***Grifola frondosa* (Fr.) S.F.Gray**
Varietal Denomination: Grifon-8go

(71) Applicant: HOKUTO CORPORATION, Nagano (JP)

(72) Inventors: Megumi Takano, Nagano (JP); Ayumi Nakagoshi, Nagano (JP)

(73) Assignee: HOKUTO CORPORATION, Nagano (JP)

( * ) Notice: Subject to any disclaimer, the term of this patent is extended or adjusted under 35 U.S.C. 154(b) by 0 days.

(21) Appl. No.: 16/602,360

(22) Filed: Sep. 23, 2019

(65) Prior Publication Data

US 2020/0100415 P1 Mar. 26, 2020

(30) Foreign Application Priority Data

Sep. 26, 2018 (JP) ..... 33394

(51) Int. Cl.
*A01H 15/00* (2006.01)

(52) U.S. Cl.
USPC ..... Plt./394
CPC ..... *A01H 15/00* (2013.01)

(58) Field of Classification Search
USPC ..... Plt./394
CPC ..... A01H 15/00
See application file for complete search history.

(56) References Cited

PUBLICATIONS

PLUTO UPOVROM Plant Variety Database Citation for 'Grifon-8go' as per JP PBR 33394; Sep. 27, 2018; 1 page.*
PLUTO UPOVROM Plant Variety Database Citation for 'Grifon-8go' as per JP PBR 33394; Sep. 26, 2018; 1 page.*

* cited by examiner

*Primary Examiner* — Kent L Bell
(74) *Attorney, Agent, or Firm* — Taro Yaguchi

(57) ABSTRACT

The present variety of mushroom named 'Grifon-8go' was cultivated by the gathering and repeated breeding of Maitake mushrooms having dominant traits, which has good qualitative character and appearance, a strong curving cap of high quality, and enhanced cultivation. This edible mushroom is exquisite in stability, reproducibility and uniformity when being produced.

19 Drawing Sheets

BACKGROUND OF THE INVENTION

This invention relates to a new and distinct variety of Maitake mushroom, *Grifola frondosa* (Fr.) S.F.Gray. This new variety named 'Grifon-8go' cultivated by repeated breeding of Maitake mushrooms having dominant traits, which has a strong curving cap, enhanced cultivation stability, and a high-yield, and ensures presentable stability, reproducibility, and uniformity.

Maitake (*Grifola frondosa*) has long been a popular edible mushroom in Japan, and in recent years, its health benefits have attracted attention and demand for the mushroom is expanding. In the early days of artificial cultivation becoming possible, the difficulty in artificially controlling the cultivation environment suitable for cultivation of maitake had made mass production of the mushroom difficult. Therefore, we developed a variety that is easy to grow, with improved quality, taste, and keeping quality named 'Hokuto NT-100gokin' (U.S. Plant Pat. No. 17,984 P3). Subsequently, with the aim of resolving a problem of easy discoloration and poor appearance of the back of the cap present in 'Hokuto NT-100gokin', cross-breeding was repeatedly conducted, and a variety with a white back of the cap named 'Grifon120' was developed (U.S. Plant Pat. No. 21,575 P3). However, due to the color of the surface of the cap being thin, the 'Grifon120' mushroom had a problem of declining freshness, and as a result of further product development, a variety with an enriched cap color and excellent cultivatability named 'Grifon-7' was developed (U.S. Plant Pat. No. 25,856 P3).

'Grifon-7' has no curving of the edge of the cap, and there was the problem of the cap being easily broken during packaging. Therefore, continuing breed improvement was conducted by cross breeding so as to improve this problem and further enhance cultivation stability, and a new variety, 'Grifon-8go', with a strong cap, high quality and excellent cultivatability was developed. Subsequently, the stability, reproducibility and uniformity of the variety were verified, and cultivation was completed.

SUMMARY OF THE INVENTION

The present invention is a new and distinct variety of mushroom characterized particularly by its good qualitative character and appearance, a strong curving cap of high quality, which can be cultivated by gathering and repeated breeding of fungal strains having dominant traits and is exquisite in stability, reproducibility and uniformity when being produced. This novel and distinct variety of mushroom is identified as 'Grifon-8go'.

DETAILED DESCRIPTION OF THE INVENTION

'Grifon-8go' mushroom was discovered at Mushroom Research Laboratory in Nagano-shi, Nagano, Japan where the temperature, humidity and carbon dioxide gas concentration are controlled. 'Grifon-8go' was asexually reproduced by inoculating on a potato dextrose agar with hyphae and incubating in a culture room set at 25° C. The history of the 'Grifon-8go' mushroom in terms of improvement period and the like are set forth in the following chronological list of each stage of variety improvement:

December 2011: 'MH182239' and 'MH182242' strains were crossed, and 'Grifon-7' was obtained September 2014: 'Grifon120' and 'MH182264' strains were crossed, and 'MH182265' was obtained July 2017: 'Grifon-7' and 'MH182265' strains were crossed, and the excellent strain 'MH182266' was obtained September 2018: Growing test was repeatedly conducted on 'MH182266' and since distinguishability, stability, reproducibility and uniformity were confirmed, the strain was named 'Grifon-8go' and cultivation was completed. Dual culture performed for 'Grifon-8go' and 'Grifon120' and dual culture performed for 'Grifon-8go' and 'Mori51go' showed formation of a zone line (FIGS. 3A, 3B, 4A, and 4B). Applied for registration of a new variety to the Ministry of Agriculture, Forestry and Fisheries of Japan. Registered the Application No. 33394 on Sep. 26, 2018.

In morphological characteristics, 'Grifon-8go' has a thicker cap (2.82 mm) than that of the parent variety, 'Grifon-7' (1.79 mm). And the shape of the cross section of the fungus is angled 45 degrees downward in 'Grifon-8go', while it is horizontal in the parent variety, 'Grifon-7'. Also, the color of the back of the fungus is white on 'Grifon-8go'; on the other hand, it is slightly yellow on the parent variety, 'MH182265'.

Figure 1:
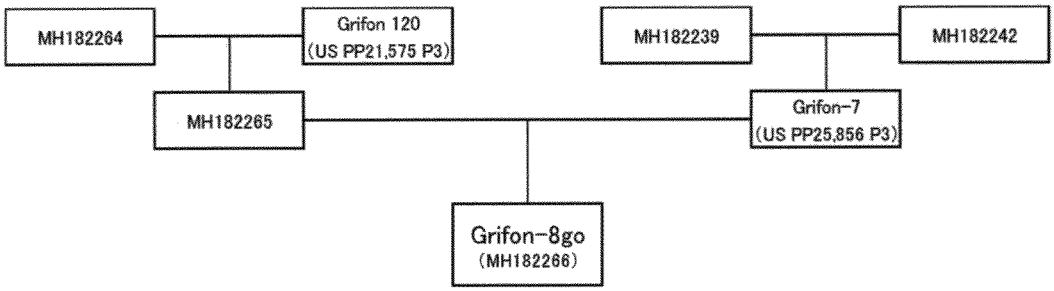
FIG. 1 shows a phylogenetic tree illustrating the antecedents of 'Grifon-8go'.
Figure 2B:
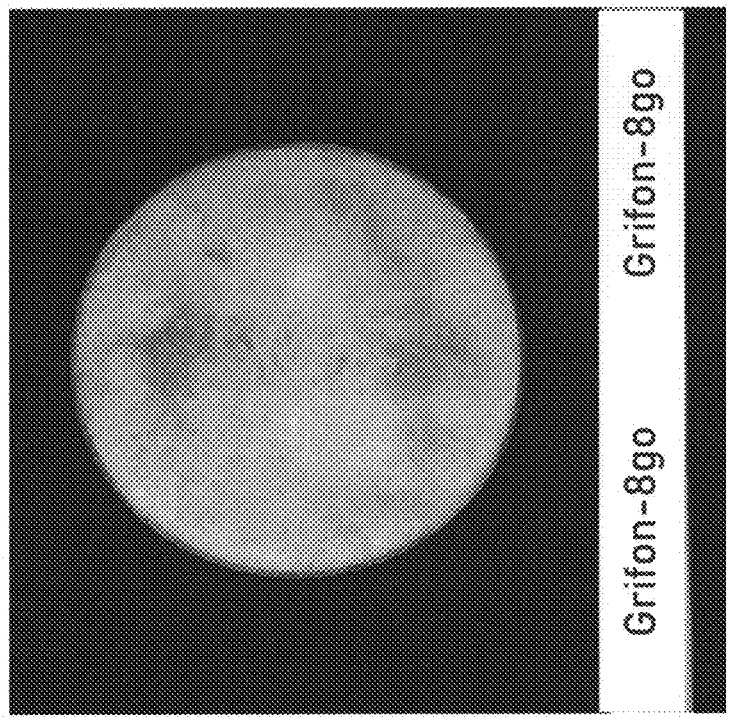
FIGS. 2A and 2B respectively show front and back images of a dual-culture of 'Grifon-8go' colony.
Figure 2A:
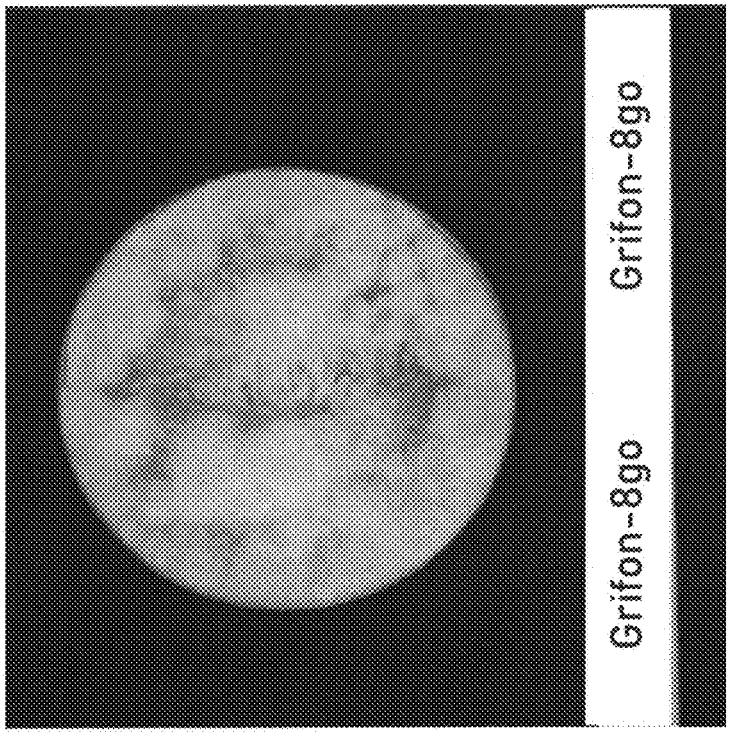
Figure 3B:
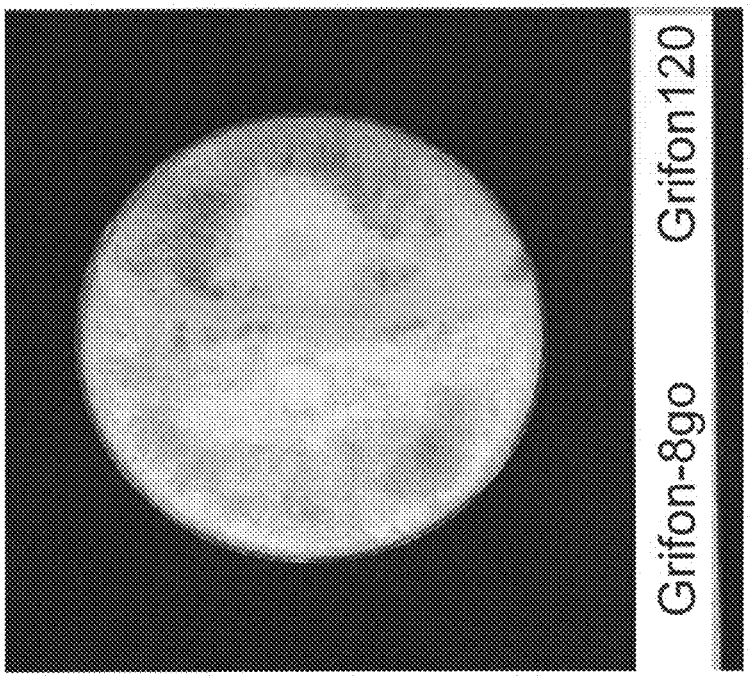
FIGS. 3A and 3B respectively show front and back images of a dual-culture of 'Grifon-8go' and 'Grifon120'.
Figure 3A:
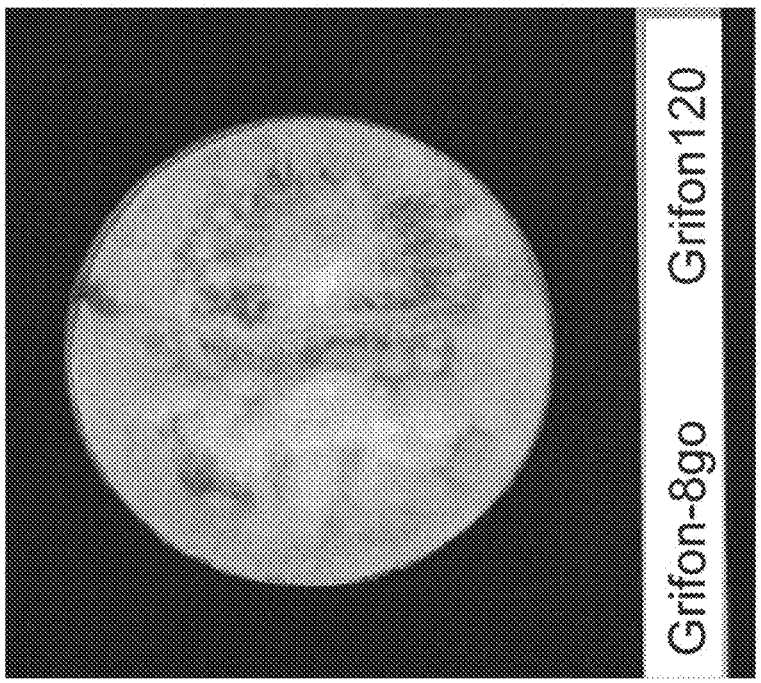
Figure 4B:
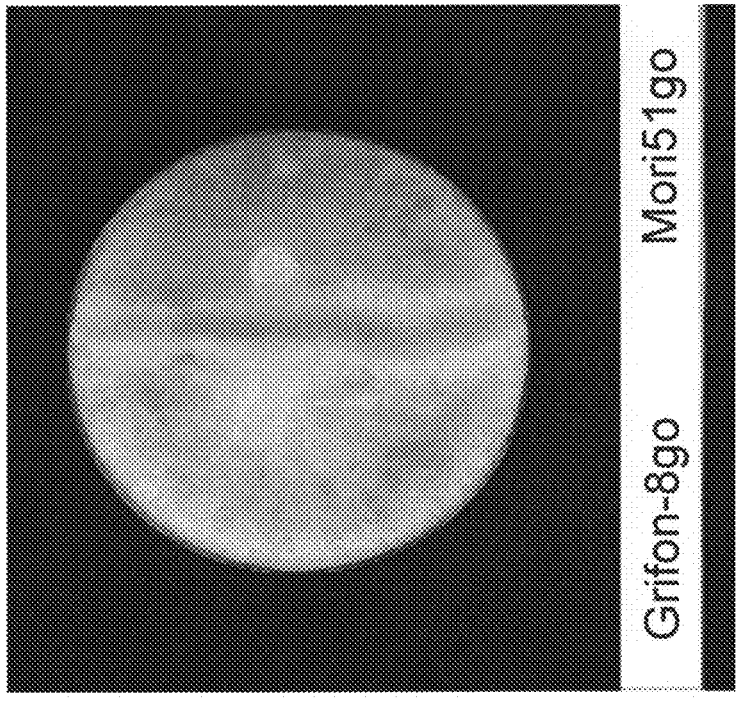
FIGS. 4A and 4B respectively show front and back images of a dual-culture of 'Grifon-8go' and 'Mori51go'.
Figure 4A:
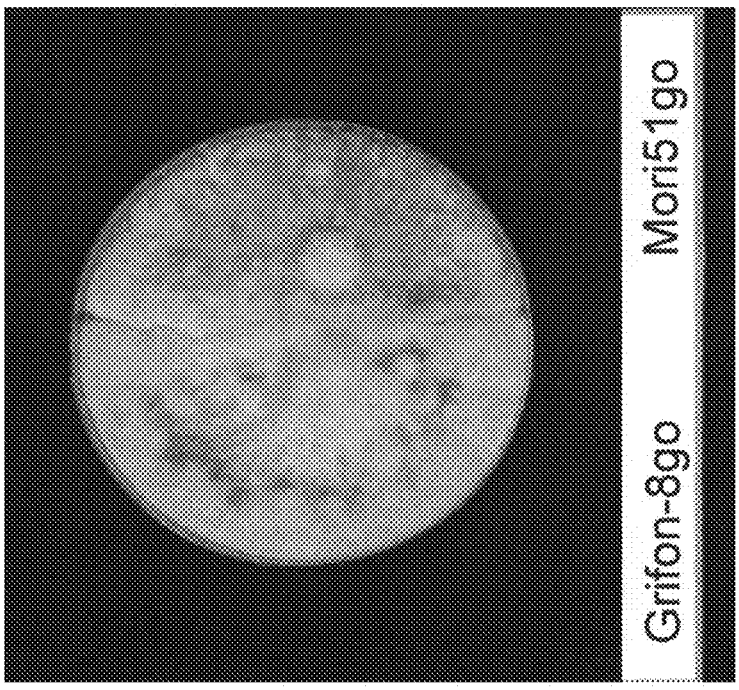
Figure 5B:
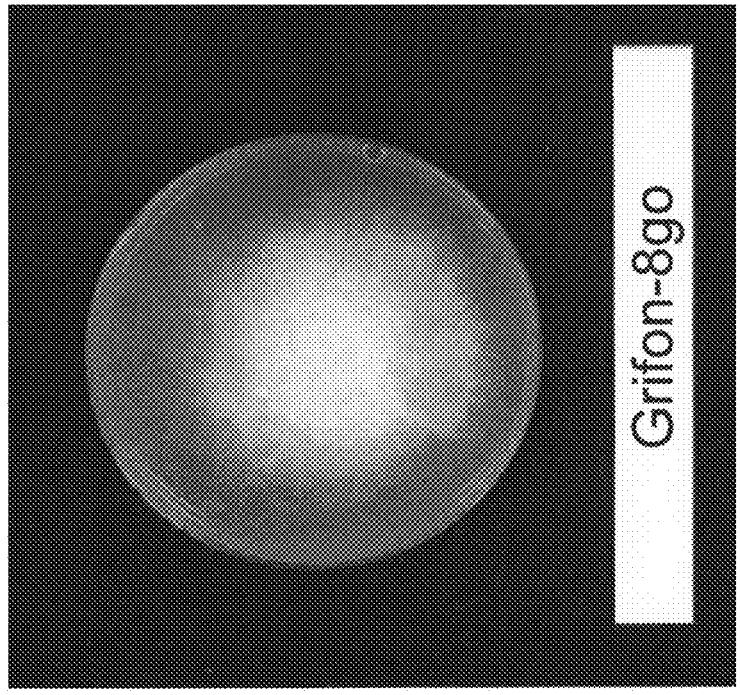
FIGS. 5A and 5B respectively show front and back images of fungal flora of 'Grifon-8go'.
Figure 5A:
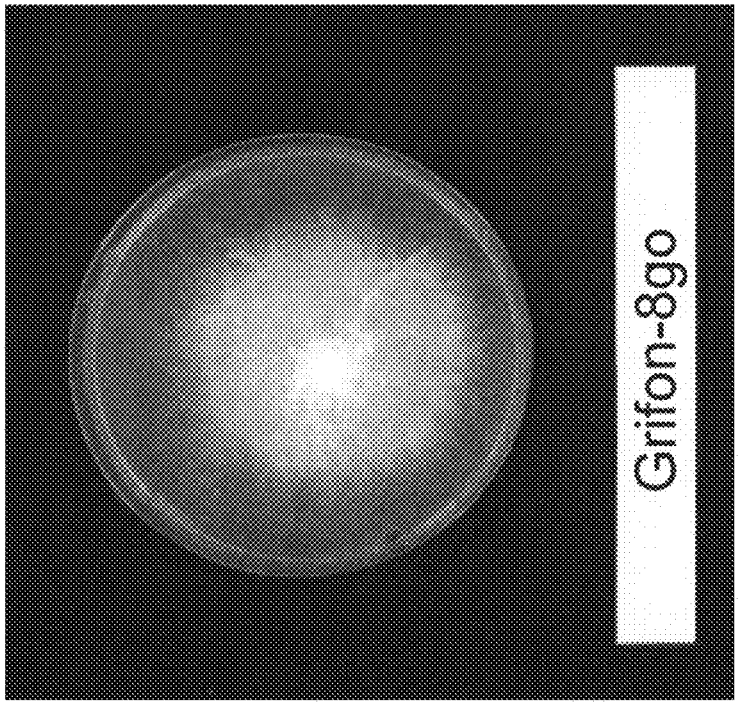
Figure 6B:
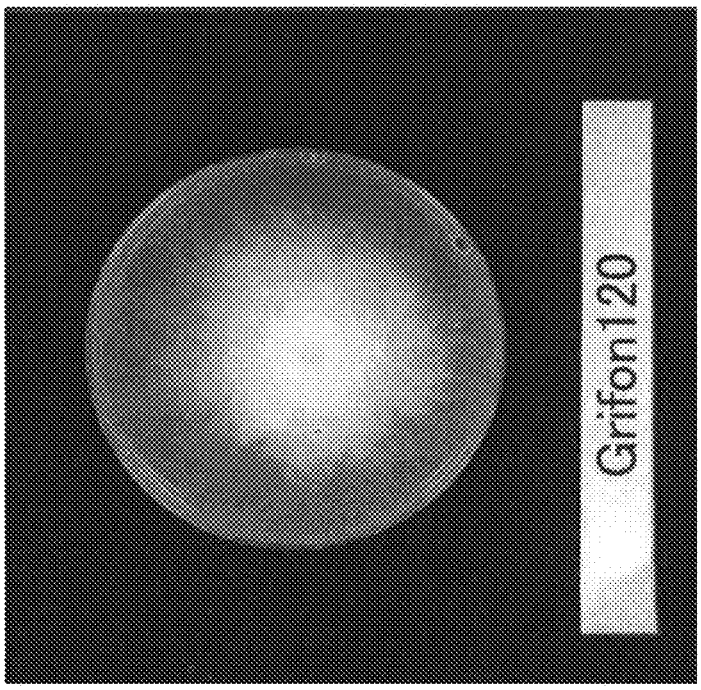
FIGS. 6A and 6B respectively show front and back images of fungal flora of 'Grifon120'.
Figure 6A:
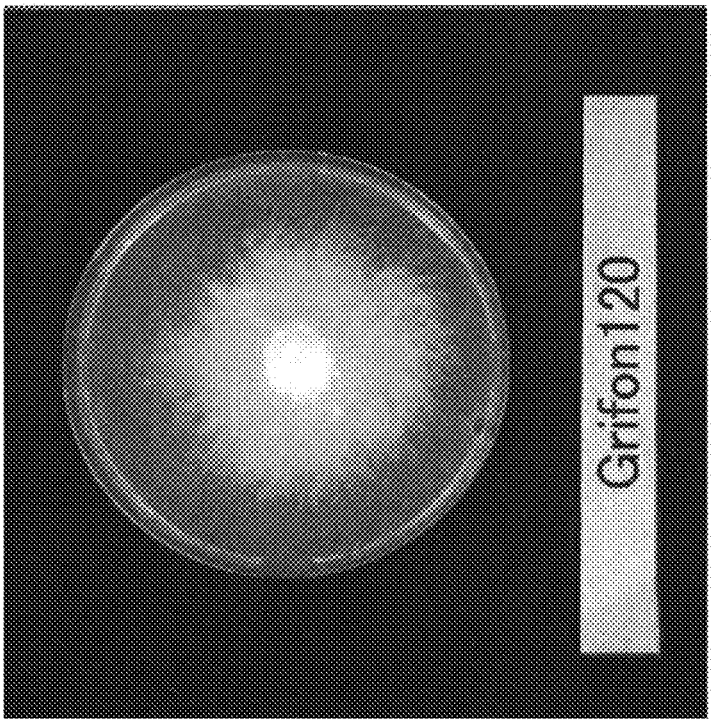
FIG. 6A Prior Art
Figure 7B:
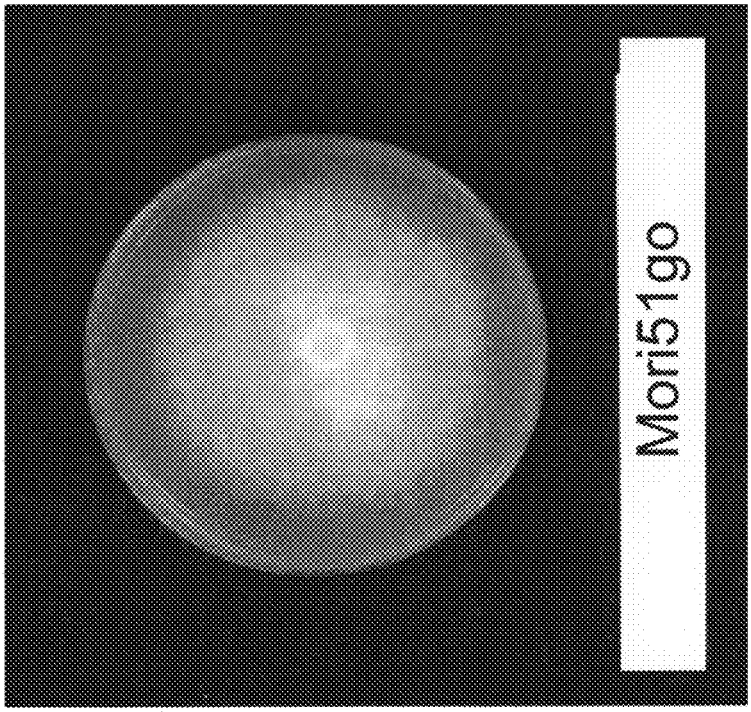
FIGS. 7A and 7B respectively show front and back images of fungal flora of 'Mori51go'.
Figure 7A:
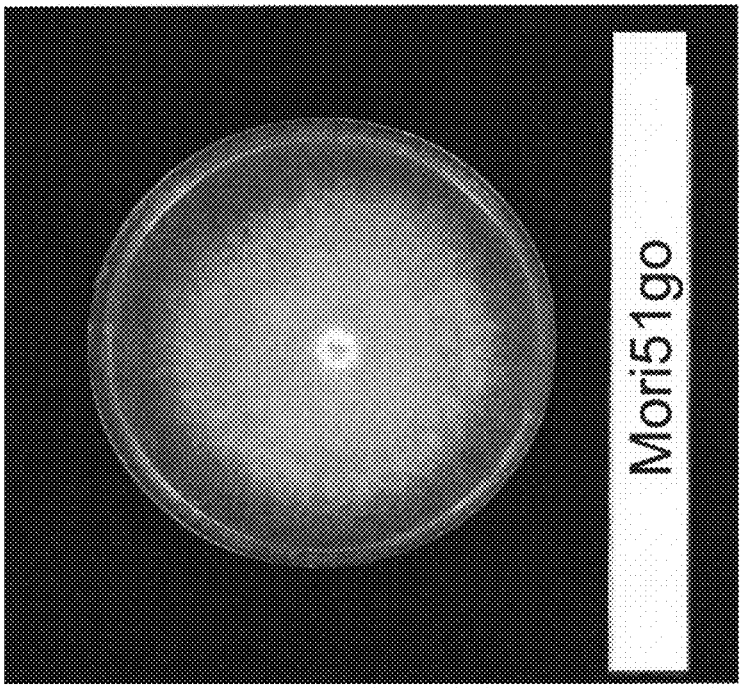
FIG. 7A Prior Art
Figure 8:
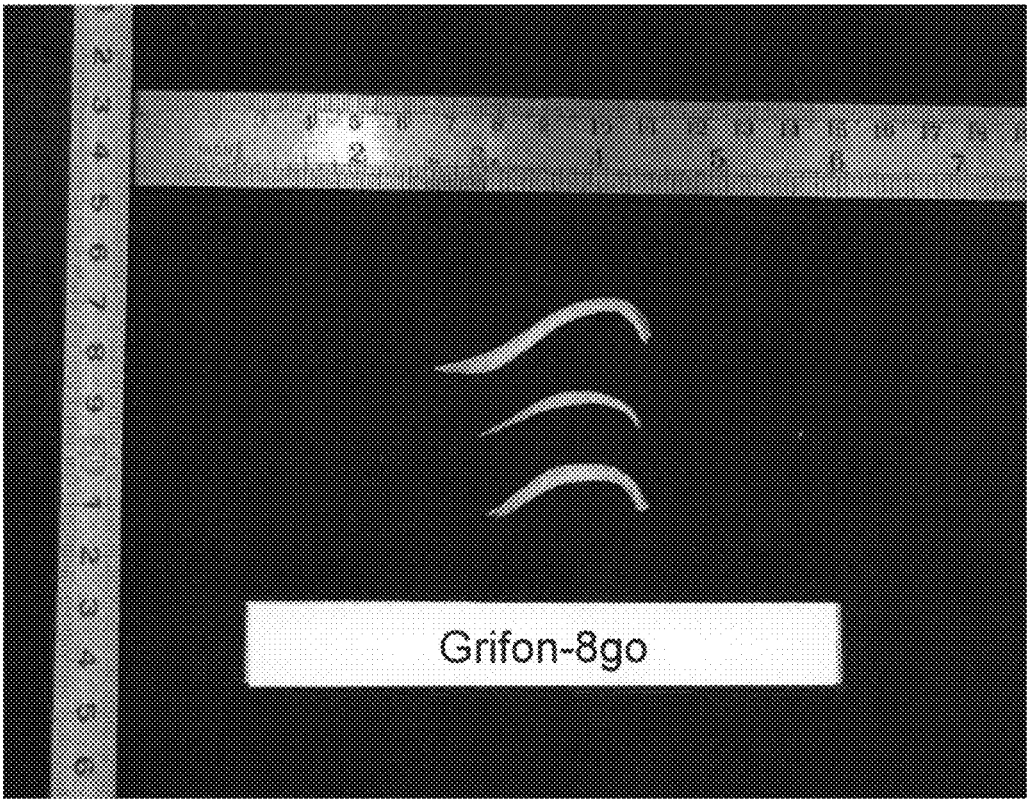
FIG. 8 shows an image of cap thickness and shape at the cross section of the cap of 'Grifon-8go'.
Figure 9:
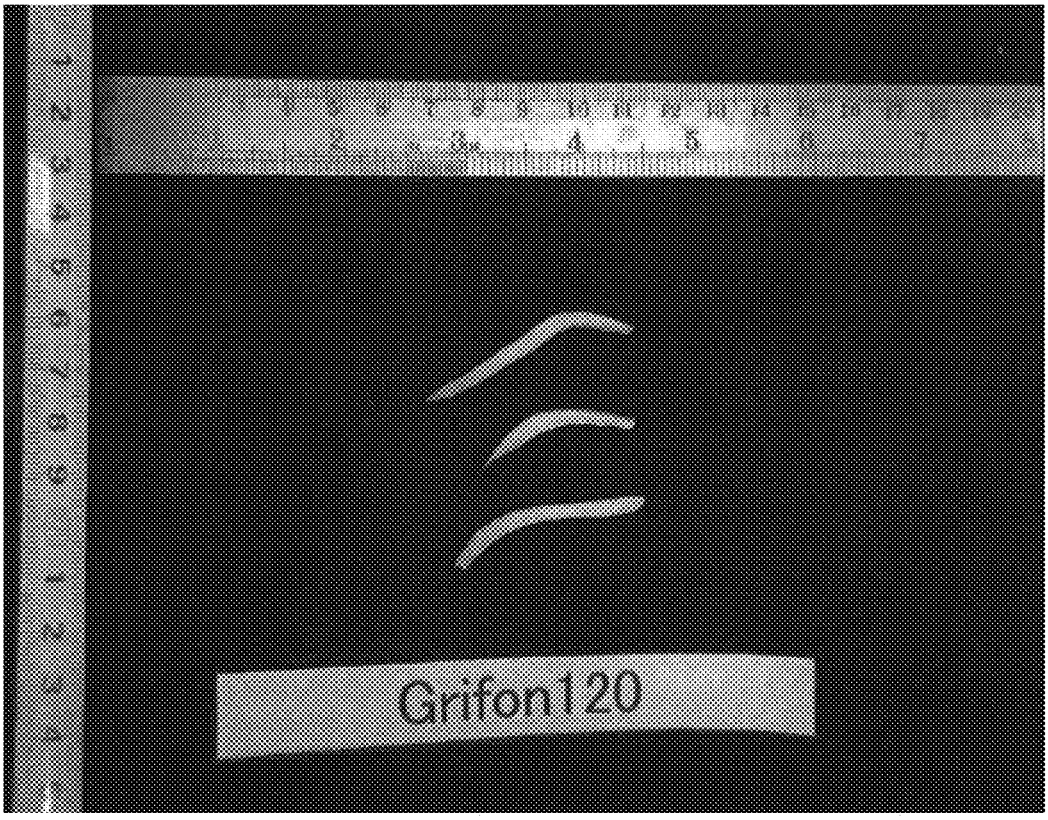
FIG. 9 Prior Art
FIG. 9 shows an image of cap thickness and shape at the cross section of the cap of 'Grifon120'.
Figure 10:
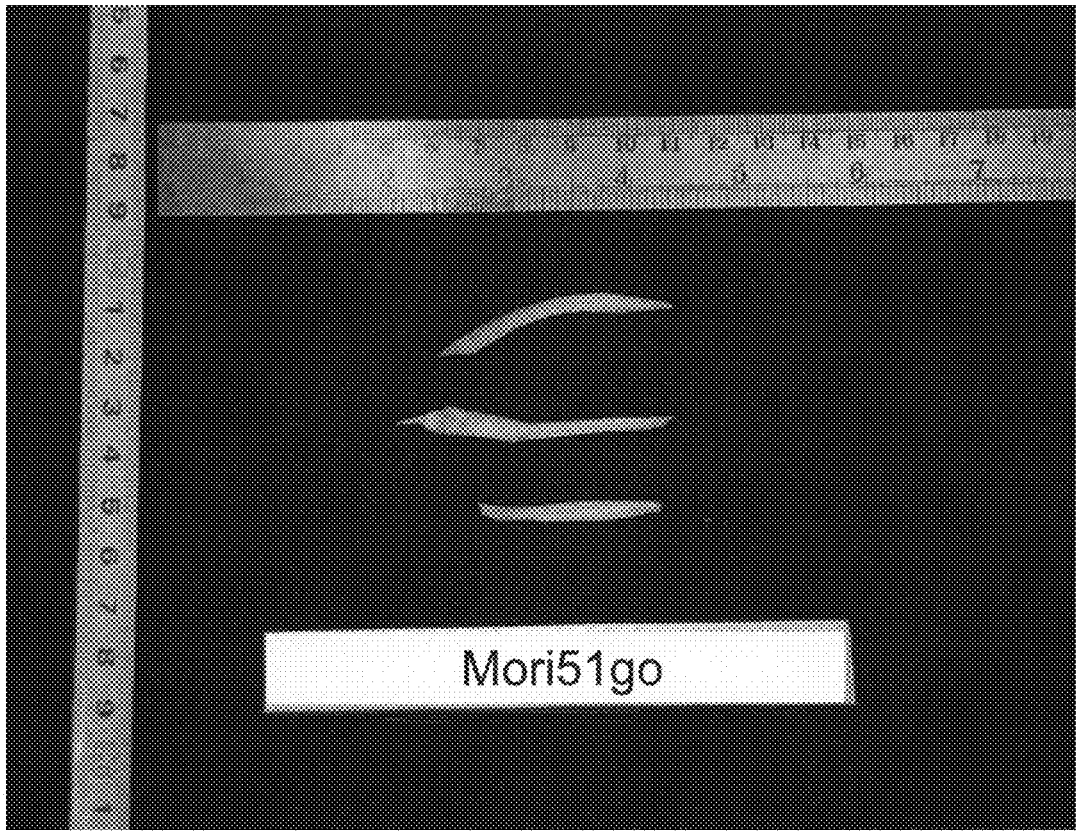
FIG. 10 Prior Art
FIG. 10 shows an image of cap thickness and shape at the cross section of the cap of 'Mori51go'.
Figure 11:
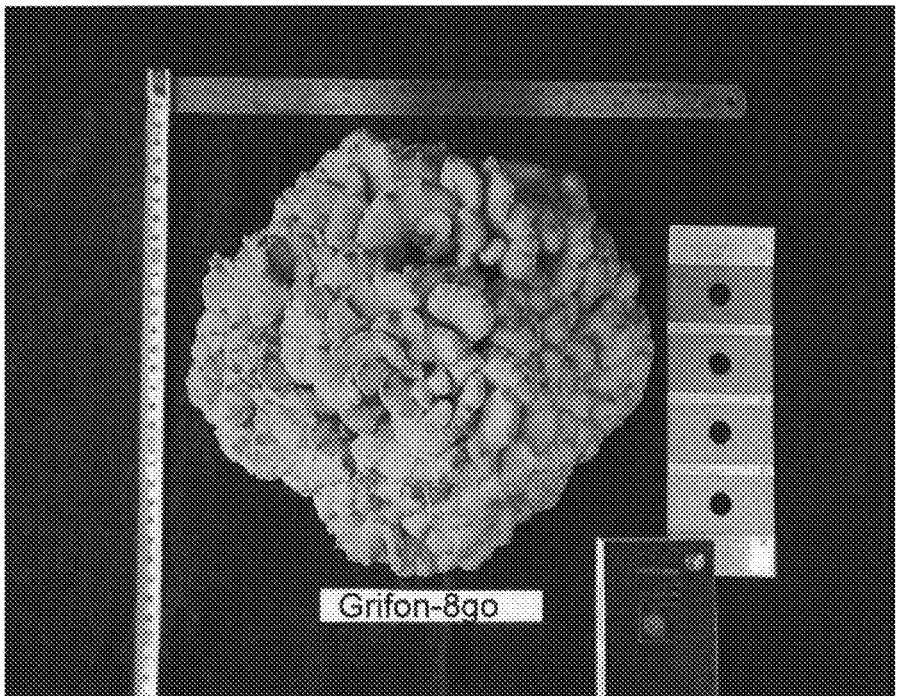
FIG. 11 shows an image of the diameter of the fruit body cluster, surface color of cap, and ring shape of 'Grifon-8go'.
Figure 12:
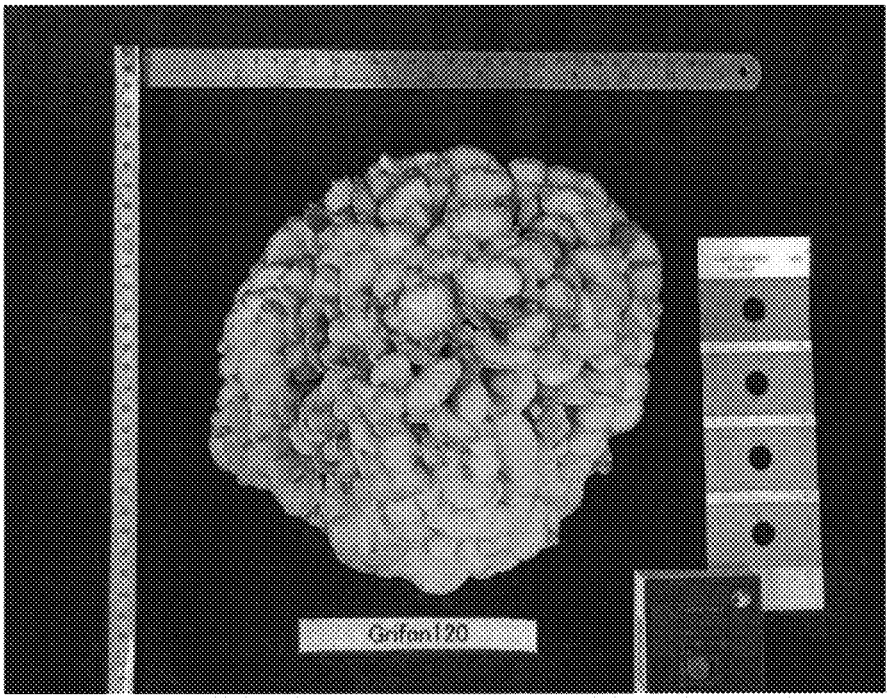
FIG. 12 Prior Art
FIG. 12 shows an image of the diameter of the fruit body cluster, surface color of cap, and ring shape of 'Grifon120'.
Figure 13:
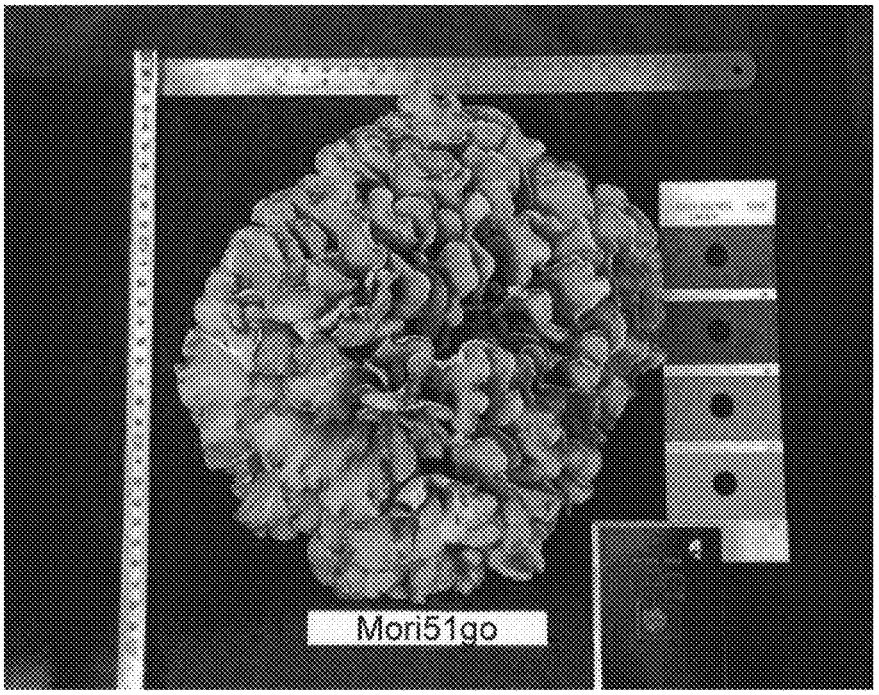
FIG. 13 Prior Art
FIG. 13 shows an image of the diameter of the fruit body cluster, surface color of cap, and ring shape of 'Mori51go'.
Figure 14:
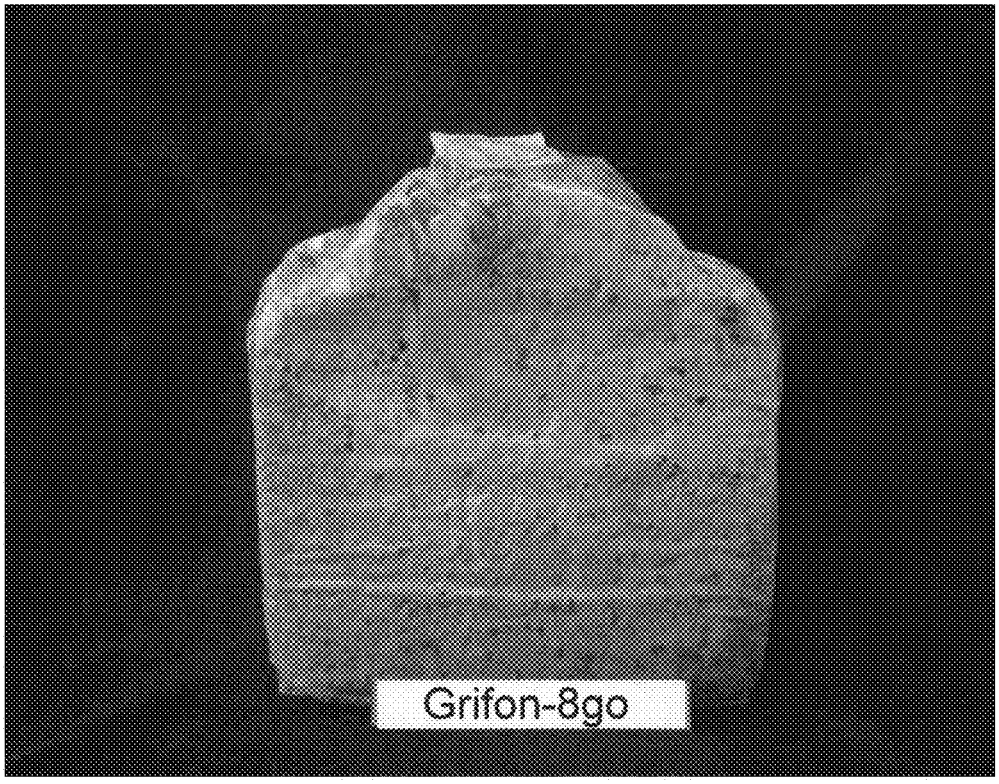
FIG. 14 shows an image of the formation and color of the surface coating of the culturing mushroom bed of 'Grifon-8go'.
Figure 15:
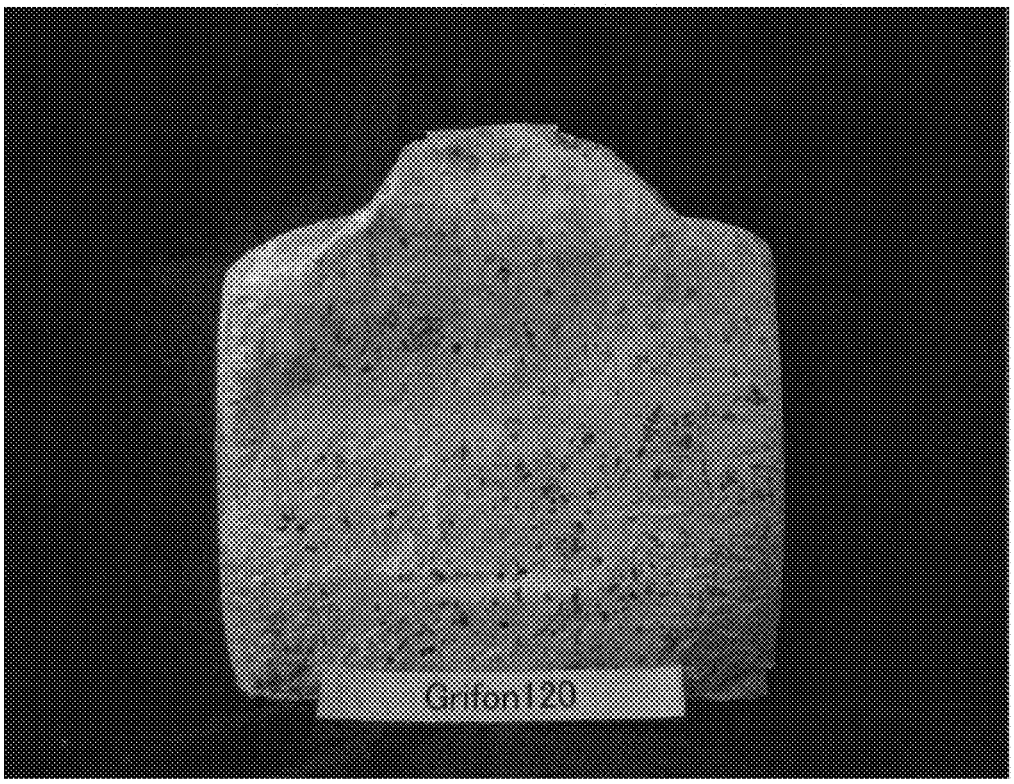
FIG. 15 Prior Art
FIG. 15 shows an image of the formation and color of the surface coating of the culturing mushroom bed of 'Grifon120'.
Figure 16:
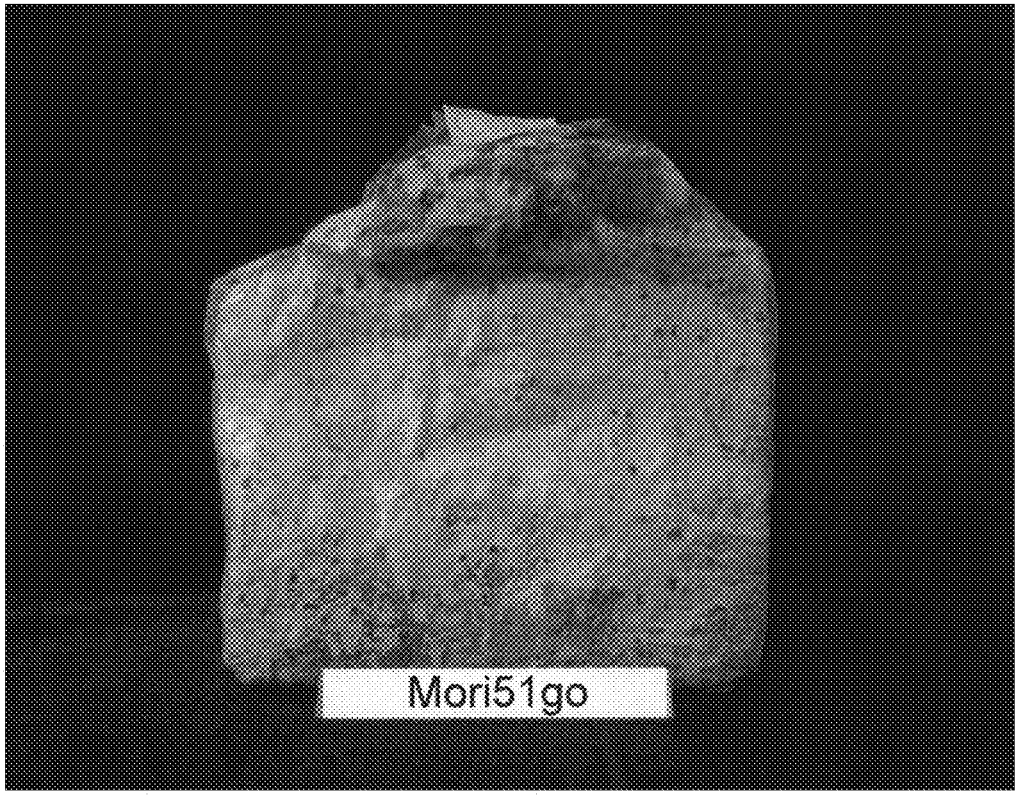
FIG. 16 Prior Art
FIG. 16 shows an image of the formation and color of the surface coating of the culturing mushroom bed of 'Mori51go'.
Figure 17:
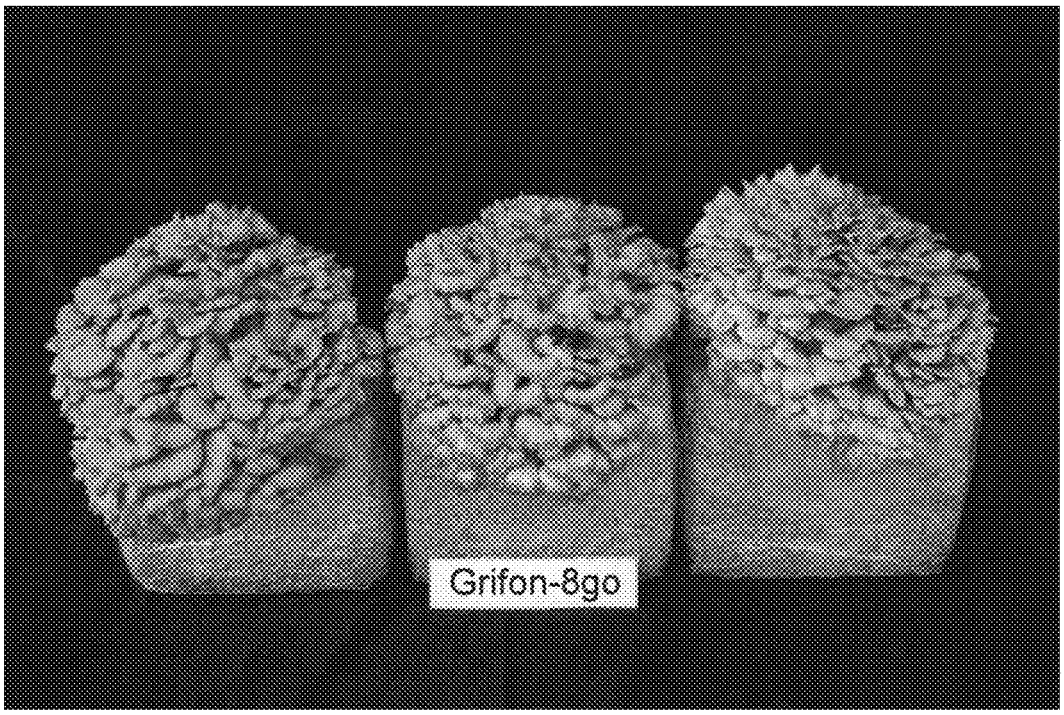
FIG. 17 shows an image of fruit bodies of 'Grifon-8go'.
Figure 18:
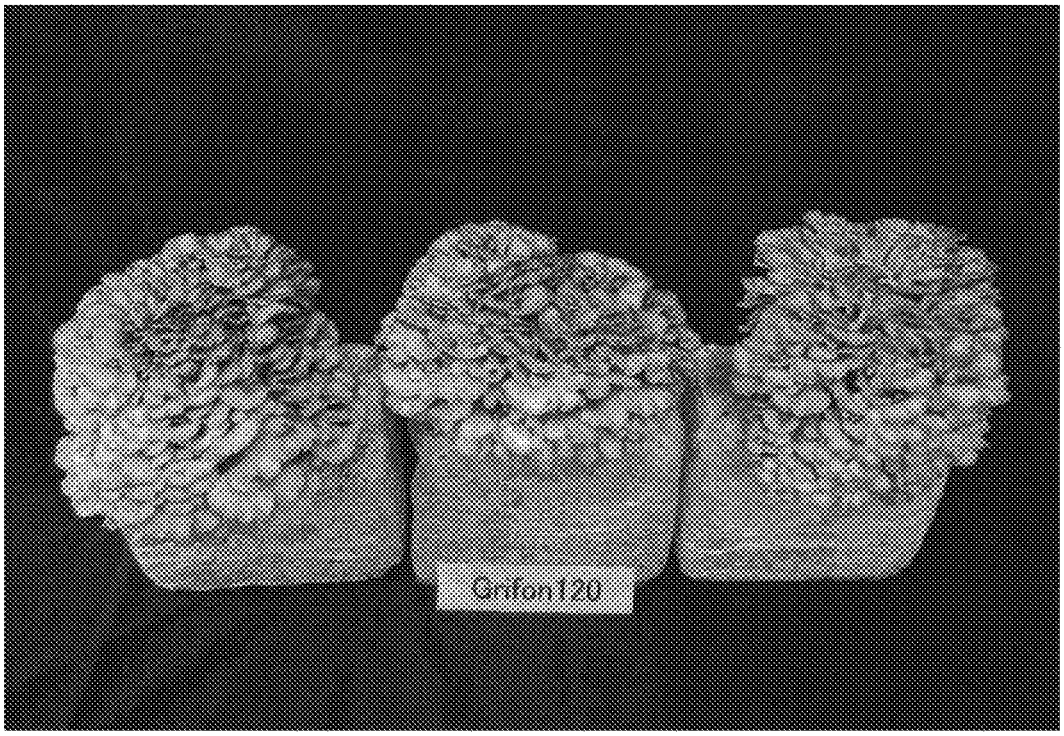
FIG. 18 Prior Art
FIG. 18 shows an image of fruit bodies of 'Grifon120'.
Figure 19:
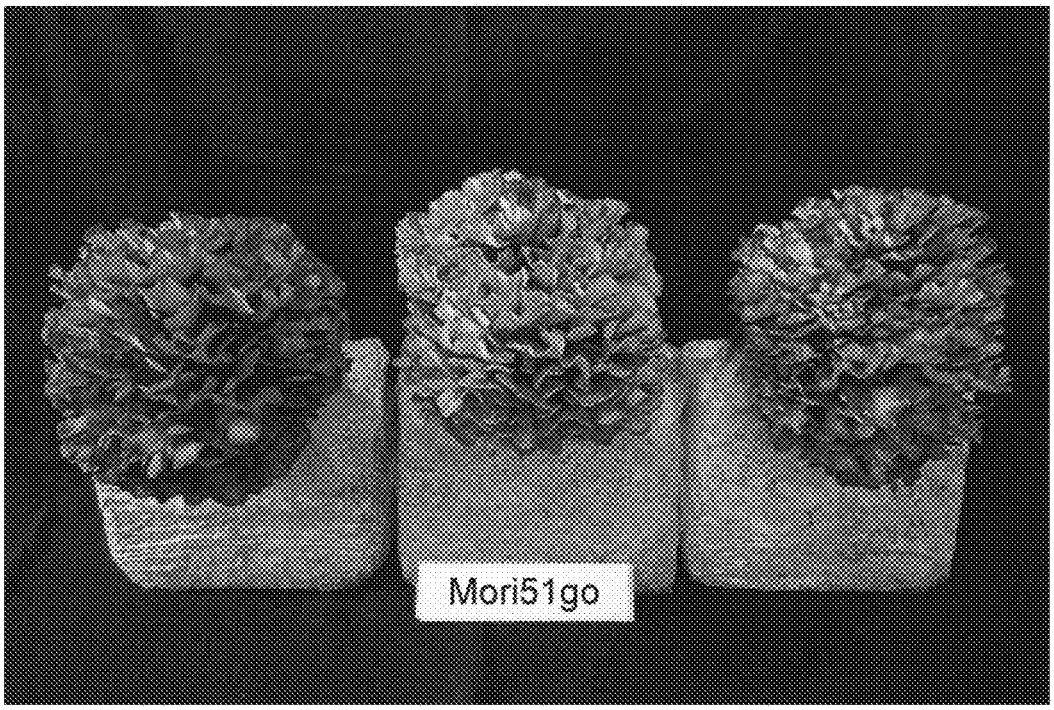
FIG. 19 Prior Art
FIG. 19 shows an image of fruit bodies of 'Mori51go'.

The above crossing is summarized in the phylogenetic tree illustrated in FIG. 1.

The 'Grifon-8go' mushroom has the following characteristics: a strong curving cap, enhanced cultivation stability, and a high-yield.

(1) Comparison with Analogous Variety by Dual Culture

Dual culture was performed for the 'Grifon-8go' mushroom and similar varieties so as to examine the tactile reaction.

Study Method:

In an examination for tactile reaction, a potato dextrose agar medium was used, and the 'Grifon-8go' mushroom and similar varieties were inoculated thereon face to face at an interval of 3 cm, and then culture was performed at 25° C. for 21 days to examine the presence or absence of a tactile reaction.

Strain Used:

'Grifon-8go': Present variety

'Grifon120': Variety similar to the present variety

'Mori51go': Variety similar to the present variety

Results:

A zone line was formed between 'Grifon-8go' and similar varieties 'Grifon120' and 'Mori51go', respectively (Table 1, FIGS. 3A, 3B, 4A, and 4B). This clearly shows that the present mushroom is a new variety.

TABLE 1

Results of dual culture

| | Similar variety 'Grifon120' | Similar variety 'Mori51go' | Present variety 'Grifon-8go' |
|---|---|---|---|
| 'Grifon-8go' | + | + | – |

+ is present and – is absent.

(2) Culture Characteristics of 'Grifon-8go'

(2)-1. Hyphae Temperature Adaptability

Study Method:

After inoculating an agar piece of the 'Grifon-8go' having a diameter of 5 mm and agar pieces of similar varieties in potato dextrose agar medium, preculture was performed at 25° C. for 4 days and hyphae were regenerated (about 10 mm in diameter), and then culture was performed for 7 days at intervals of 5° C. between 10° C. and 30° C. The average daily hyphae growth rate was calculated based on a hyphae growth rate for seven days of the culture. 'Grifon-8go' was asexually reproduced by inoculating on a potato dextrose agar at Mushroom Research Laboratory in Nagano-shi, Nagano, Japan.

Study Results:

'Grifon-8go''s hyphae growth rate was found to be faster than the similar variety 'Grifon120' at 10° C., 15° C., 20° C., 30° C. (See Table 2).

(2)-2. Comparison of Fungal Flora

Study Method:

After inoculating an agar piece of the 'Grifon-8go' having a diameter of 5 mm and agar pieces of similar varieties having a diameter of 5 mm on a potato dextrose agar medium, culture was performed at 25° C. for 14 days.

Study Results:

Regarding thickness of the fungal flora, the flora was thinner in the similar variety 'Mori51go' than in 'Grifon-8go' (See Table 2).

(3) Morphological Characteristics of the 'Grifon-8go' Mushroom in a Cultivation Example Cultivation Method:

Container: A polypropylene cultivation bag (Square, capacity: 8,500-9,000 cc, caliber: 200-120 mm, height: approx. 440 mm, with aeration filter) was used. A total of 48 bags were used, and 16 bags were repeated 3 times.

Culture medium: hardwood sawdust mainly composed of beechwood, and corn bran were mixed at the dry weight ratio of 75:25, and the water content was adjusted to 60-62%. After filling 2.5 kg of medium per bag, high pressure sterilization was performed.

Starter culture: About 25 cc of sawdust starter cultures per bag was inoculated.

Culture: Culture was performed at 20° C.-25° C., 70-75% moisture, and illuminance of 200-500 lux, and the inoculum is then moved to a development room.

Growth: The inoculum and the mushroom bag are shifted to a temperature of 17° C.-18° C., 90-95% moisture, and illuminance of 500-1,500 lux, and growth is prompted. After the growth has reached the filter portion, the filter portion is removed and growth into fruiting bodies is prompted. The mushroom is harvested when the tube at the mushroom back has formed about 2-3 mm from the edge.

Cultivation Results:

Table 2 shows the characteristics of the 'Grifon-8go' and specific difference in characteristics as compared with the similar varieties when culture was performed under the abovementioned conditions.

Also, the images of the respective shape of caps, fruit body, surface colors, and ring shapes, and the images of the respective culturing mushroom beds have also been attached. (Refer to FIGS. 8 to 19).

TABLE 2

Fungus characteristics Table of Grifola frondosa (Fr.) S.F.Gray of Recording and Registration

| | Present variety | Similar variety | |
|---|---|---|---|
| | 'Grifon-8go' | 'Grifon120' | 'Mori51go' |
| Hyphae density | slightly dense | slightly dense | slightly dense |
| Developmental state of aerial hyphae | dense | dense | medium |

TABLE 2-continued

Fungus characteristics Table of Grifola frondosa (Fr.) S.F.Gray of Recording and Registration

| | Present variety | Similar variety | |
|---|---|---|---|
| | 'Grifon-8go' | 'Grifon120' | 'Mori51go' |
| Shape of the periphery of the fungal flora | heterogenous | heterogenous | heterogenous |
| Fungal flora thickness | medium | medium | thin |
| Fungal flora surface coloring | none | none | none |
| Fungal flora surface shape | smooth | smooth | smooth |
| Optimal temperature for hyphal growth | 26~28° C. | 24~26° C. | 26~28° C. |
| Hyphal growth rate | | | |
| 10° C./day | 1.72 mm | 1.28 mm | 1.45 mm |
| 15° C./day | 2.34 mm | 1.79 mm | 2.34 mm |
| 20° C./day | 3.25 mm | 2.76 mm | 3.48 mm |
| 25° C./day | 4.16 mm | 3.54 mm | 4.26 mm |
| 30° C./day | 4.03 mm | 2.96 mm | 3.95 mm |
| Fruiting body diameter | 21.36 cm | 20.25 cm | 19.89 cm |
| Size of cap (Diameter) | 33.78 mm | 31.07 mm | 37.85 mm |
| Thickness of cap | 2.82 mm | 2.66 mm | 2.46 mm |
| Shape of cap | fan form | fan form | fan form |
| Presence of lacinia on edge of cap | none | none | none |
| Color on edge of cap | N199B | N200B | 200B |
| Shape at the cross section of cap | angled 45 degrees downward | horizontal | horizontal |
| Surface color of cap | 199B | 199C | N199C |
| Fleshiness of cap | medium | medium | medium |
| Ring shape of the cap surface | periphery | periphery | periphery |
| Site of tube growth | whole cap | whole cap | whole cap |
| Form of strain base of fruit body | thick | thick | thick |
| Formation of surface coating on culturing mushroom bed | little | slightly little | medium |
| Presence of color on the surface coating of culturing mushroom bed | none | none | present |
| Period until primordial formation | 33.79 days | 36.08 days | 43.48 days |
| Period until peak growth | 43.63 days | 47.08 days | 56.33 days |
| Optimal growth temperature for fruiting body | 22-24° C. | 22-24° C. | 20-22° C. |
| Yield | 920.38 g | 835.60 g | 663.04 g |

* The employed color chart is R.H.S Colour Chart, 2007, Fifth edition, prescribed by Royal Horticultural Society, England.

What is claimed is:

1. A new, distinct variety of Maitake mushroom as substantially illustrated and described in the specification.

* * * * *